US006682640B2

United States Patent
Jain et al.

(10) Patent No.: US 6,682,640 B2
(45) Date of Patent: Jan. 27, 2004

(54) CO-FIRED OXYGEN SENSOR ELEMENTS (75) Inventors: Kailash C. Jain, Troy, MI (US); Eric Clyde, Bay City, MI (US); Da Yu Wang, Troy, MI (US); Paul Kikuchi, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 20 days.

(21) Appl. No.: 10/170,941

(22) Filed: Jun. 13, 2002

(65) Prior Publication Data

US 2003/0230484 A1 Dec. 18, 2003

(51) Int. Cl.[7] .............................................. G01N 27/407
(52) U.S. Cl. ...................... 204/429; 204/421; 204/427; 427/126.1; 427/126.3; 427/331; 427/372.2; 427/419.1; 427/419.2; 427/419.3
(58) Field of Search ................................. 204/421–429; 427/58, 126.1, 126.3, 331, 372.2, 402, 419.1, 419.2, 419.3, 430.1, 443.2

(56) References Cited

U.S. PATENT DOCUMENTS

| | | |
|---|---|---|
| 3,556,957 A | 1/1971 | Toledo et al. |
| 3,844,920 A | 10/1974 | Burgett et al. |
| 4,136,000 A | 1/1979 | Davis et al. |
| 4,169,777 A | 10/1979 | Young et al. |
| 4,277,323 A | 7/1981 | Muller et al. |
| 4,310,401 A | 1/1982 | Stahl |
| 4,318,770 A | 3/1982 | Chakupurakal |
| 4,426,253 A | 1/1984 | Kreuz et al. |
| 4,986,880 A | 1/1991 | Dorfman |
| 5,334,284 A | 8/1994 | Ngo |
| 5,372,981 A | 12/1994 | Witherspoon |
| 5,384,030 A | 1/1995 | Duce et al. |
| 5,433,830 A | 7/1995 | Kawai et al. |
| 5,443,711 A | 8/1995 | Kojima et al. |
| 5,467,636 A | 11/1995 | Thompson et al. |
| 5,602,325 A | 2/1997 | McClanahan et al. |
| 5,616,825 A | 4/1997 | Achey et al. |
| 5,733,504 A | 3/1998 | Paulus et al. |
| 6,179,989 B1 * | 1/2001 | Kennard et al. |
| 6,544,405 B2 * | 4/2003 | Clyde et al. |

OTHER PUBLICATIONS

H. Obayashi and H. Okamoto, "Low Temperature Performance of Fluoride–Ion_Treated ZrO2 Oxygen Sensor", Solid State Ionics 3/4 (1981) month unavailable pp.631–634.

* cited by examiner

Primary Examiner—T. Tung
(74) Attorney, Agent, or Firm—Jimmy L. Funke (57) ABSTRACT Disclosed herein is a method for producing a gas sensor, comprising disposing a reference electrode on a side of an electrolyte, disposing a measuring electrode on a side of the electrolyte opposite the reference electrode, disposing a first protective coating on a side of the measuring electrode opposite the electrolyte, treating the sensor with an aqueous salt solution comprising chloride and carbonate salts comprising elements selected from the group consisting of Group IA and IIA elements of the Periodic Table to form a treated sensor comprising the chloride and the carbonate salt mixture, drying the treated sensor, and disposing a second protective coating on a side of the first protective coating opposite the measuring electrode.

13 Claims, 5 Drawing Sheets

CO-FIRED OXYGEN SENSOR ELEMENTS

BACKGROUND OF THE INVENTION

Automotive vehicles with an internal combustion engine have an exhaust system including a pathway for exhaust gas to move away from the engine. Depending on the desired operating state, internal combustion engines can be operated with fuel/air ratios in which (1) the fuel constituent is present in a stoichiometric surplus (rich range), (2) the oxygen of the air constituent is stoichiometrically predominant (lean range), and (3) the fuel and air constituents satisfy stoichiometric requirements. The composition of the fuel-air mixture determines the composition of the exhaust gas.

The oxygen concentration in the exhaust gas of an engine has a direct relationship to the air-to-fuel ratio of the fuel mixture supplied to the engine. As a result, gas sensors, namely oxygen sensors, are used in automotive internal combustion control systems to provide accurate oxygen concentration measurements of automobile exhaust gases for determination of optimum combustion conditions, maximization of fuel economy, and management of exhaust emissions.

An oxygen sensor comprises an ionically conductive solid electrolyte material, a sensing electrode that is exposed to the exhaust gas and reference electrode that is exposed to a reference gas, such as air or oxygen, at known partial pressure. It operates in potentiometric mode, where oxygen partial pressure differences between the exhaust gas and reference gas on opposing faces of the electrochemical cell develop an electromotive force (EMF), which can be described by the Nernst equation:

$$E = \left(\frac{RT}{4F}\right) \ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas The large oxygen partial pressure difference between rich and lean exhaust gas conditions creates a step-like difference in cell output at the stoichiometric point.

Oxygen sensors, during operations, are subjected to varying conditions such as temperatures ranging from ambient temperatures, when the engine has not been recently run, to higher than 1,000° C. during operation. Certain properties of the sensor may be affected by the varying conditions including electrical parameters, namely voltage amplitude, response times, switching characteristics, and light-off times. As such, stable and reproducible performance of a sensor is desirable.

SUMMARY OF THE INVENTION

Disclosed herein is a method for producing a gas sensor, comprising disposing a reference electrode on a side of an electrolyte, disposing a measuring electrode on a side of the electrolyte opposite the reference electrode, disposing a first protective coating on a side of the measuring electrode opposite the electrolyte, treating the sensor with an aqueous salt solution comprising chloride and carbonate salts comprising elements selected from the group consisting of Group IA and IIA elements of the Periodic Table to form a treated sensor comprising the chloride and the carbonate salt mixture, drying the treated sensor, and disposing a second protective coating on a side of the first protective coating opposite the measuring electrode.

The above-described and other features are exemplified by the following figures and detailed description.

BRIEF DESCRIPTION OF THE DRAWINGS

Referring now to the Figures wherein the like elements are numbered alike.

DESCRIPTION OF THE PREFERRED EMBODIMENTS

Although described in connection with an oxygen sensor, it is to be understood that the sensor, which can comprise any geometry (e.g., conical, flat plate, planar, and the like) could be a nitrogen oxide sensor, hydrogen sensor, hydrocarbon sensor, or the like. Furthermore, while oxygen is the reference gas used in the description disclosed herein, it should be understood that other gases could be employed as a reference gas.

The method for producing a gas sensor comprises disposing a reference electrode on a side of an electrolyte, disposing a measuring electrode on a side of the electrolyte opposite the reference electrode, disposing a first protective coating on a side of the measuring electrode opposite the electrolyte, treating the sensor with an aqueous salt solution comprising chloride and carbonate salts comprising elements selected from the group consisting of Group IA and IIA elements of the Periodic Table to form a treated sensor comprising the chloride and the carbonate salt mixture, drying the treated sensor, and disposing a second protective coating on a side of the first protective coating opposite the measuring electrode.

Figure 1A:
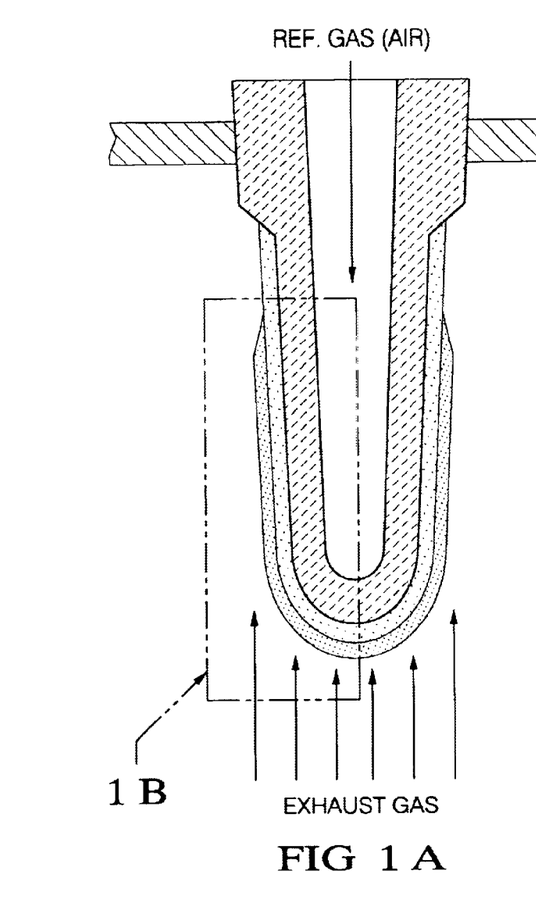
FIG. 1A is a cross-sectional view of a conical-type oxygen sensor.
Figure 1B:
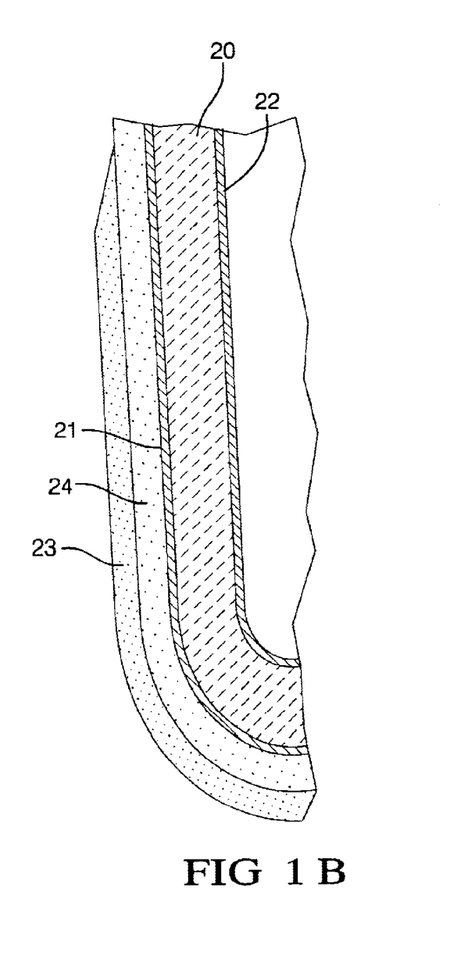
FIG. 1B shows an inset of FIG. 1A.

FIG. 1 represents an exemplary embodiment of the sensor. FIG. 1 shows a conical-type oxygen sensor (32) with a reference electrode (22) disposed on electrolyte (20), a measuring electrode (21) disposed on a side of electrolyte (20) opposite reference electrode (22), a first protective coating (24) disposed on a side of measuring electrode (21) opposite electrolyte (20), and a second protective coating (23) disposed on a side of first protective coating (24) opposite measuring electrode (21).

The electrolyte (20), which is preferably a solid electrolyte, can comprise any material that is capable of permitting the electrochemical transfer of oxygen ions while inhibiting the physical passage of exhaust gases. Possible electrolyte materials include, but are not limited to, zirconia, ceria, calcia, yttria, lanthana, magnesia, and the like, as well as combinations comprising at least one of the foregoing electrolyte materials, of which zirconia is preferred. Also preferred, is an electrolyte comprising zirconia which is either partially (preferred) or fully stabilized with calcium, barium, yttrium, magnesium, aluminum, lanthanum, cesium, gadolinium, and the like, and oxides thereof, as well as combinations comprising at least one of the foregoing electrolyte materials.

Disposed on a side of the electrolyte is reference electrode (22). Reference electrode (22) can comprise any catalyst capable of ionizing oxygen, including but not limited to, metals such as platinum, palladium, gold, osmium, rhodium, iridium, ruthenium, zirconium, yttrium, cerium, calcium, aluminum, and the like, as well as alloys, oxides, and combination comprising at least one of the foregoing catalysts. Reference electrode (22) may optionally be applied in the form of a metal ink or paste. The metal ink preferably comprises noble metals including platinum (Pt), rhodium (Rh), palladium (Pd), and alloys thereof, of which platinum is preferred.

The metal ink further comprises an electrolyte material. Suitable electrolyte materials include all those materials suitable for electrolyte (20), of which zirconia, partially or fully stabilized with calcium oxide (CaO), yttrium oxide ($Y_2O_3$), ytterbium (III) oxide ($Yb_2O_3$), scandium oxide ($Sc_2O_3$), and the like, as well as compositions comprising at least one of the foregoing stabilizers, is preferred. The metal ink optionally comprises a fugitive material. Suitable fugitive materials include graphite, carbon black, starch, nylon, polystyrene, latex, other—soluble organics (e.g., sugars and the like) and the like, as well as compositions comprising at least one of the foregoing fugitive materials. The electrolyte and fugitive materials create uniform pores during sintering to maintain gas permeability and increase catalytically active surface area. The electrolyte and fugitive materials additionally provide catalytic regions at the electrode-sensor electrolyte interface to extend performance of the sensor down to 400° C.

The metal ink may be disposed onto the electrolyte body using any suitable application process including thin or thick film deposition techniques. Suitable deposition techniques include spraying, spinning and dip-coating, with dip-coating being preferred. The thickness of the metal ink disposed on the electrolyte may be varied depending on the application method and durability requirements. The thickness of the metal ink is controlled by dipping the electrolyte in the metal ink and then regulating the dwell time in the ink suspension and the rate at which the electrolyte is withdrawn. Electrode durability increases with thickness, but at the cost of a decreased sensor sensitivity. Thus, a balance between durability and sensitivity exists, and as such, the desired balance may be achieved by controlling the thickness of the metal ink during deposition.

Preferably, the thickness of the electrode is less than or equal to about 10 micrometers ($\mu$m), with less than or equal to about 7 $\mu$m especially preferred, and less than or equal to about 5 $\mu$m most preferred. Also preferred is an electrode thickness of greater than or equal to about 0.1 $\mu$m, with greater than or equal to about 1 $\mu$m more preferred, and greater than or equal to about 3 $\mu$m most preferred.

Disposed on a side of electrolyte (20) opposite reference electrode (22) is measuring electrode (21). As with reference electrode (22), measuring electrode (21) may comprise a metal ink or paste disposed onto the electrolyte using thin or thick film deposition techniques including spraying, spinning, and dip-coating, of which dip-coating is preferred. The metal ink may similarly comprise a noble metal catalyst, an electrolyte and a fugitive material. As with reference electrode (22), the thickness of measuring electrode (21) can be varied by regulating the amount of metal ink disposed on the electrolyte. As such, differing electrode morphologies may be achieved by controlling the thickness of the metal ink disposed to form measuring electrode (21).

Disposed on a side of measuring electrode (21) opposite electrolyte (20) is first protective coating (24). First protective coating (24) may comprise a spinel (e.g., magnesium aluminate), alumina, zirconia, aluminum oxide, carbon black, and organic binders, as well as combinations comprising at least one of the foregoing materials. Preferably, the first protective coating comprises a porous ceramic material comprising aluminum oxide, carbon black, and organic binders. The carbon black acts as a fugitive to allow for effective pore formation in the first protective coating.

First protective coating (24) may be disposed using thin or thick film deposition techniques including sputtering, electron beam evaporation, chemical vapor deposition, screen printing, pad printing, ink jet printing, spinning, spraying, including flame spraying and plasma spraying, dip-coating and the like, of which dip-coating is preferred. The first protective coating may have a thickness of up to about 500 $\mu$m, with less than or equal to about 400 $\mu$m preferred.

After deposition of the first protective coating, the sensor may be sintered. Sintering occurs at temperatures up to about 1,550° C., with less than or equal to about 1,520° C. preferred, and less than or equal to about 1,510° C. more preferred. Also preferred is sintering at a temperature of greater than or equal to about 1,475° C., with greater than or equal to about 1,485° C. more preferred, and greater than or equal to about 1,490° C. especially preferred. Sintering is conducted for a duration of up to about 180 minutes, with less than or equal to about 160 minutes preferred, and less than or equal to about 140 minutes more preferred. Also preferred is sintering conducted for a duration of greater than or equal to about 10 minutes, with greater than or equal to about 50 minutes more preferred, and greater than or equal to about 100 minutes especially preferred. Sintering at the proper temperature and for the appropriate duration allows for the production of finely dispersed, uniform pores extending through first protective coating (24) and measuring electrode (21) to electrolyte (20).

The sensor is treated with an aqueous salt solution. The aqueous salt solution comprises salts of chlorides and carbonates in combination with elements selected from Group IA or IIA of the Periodic Table. Suitable elements include sodium (Na), potassium (K), lithium (Li), magnesium (Mg), calcium (Ca), strontium (Sr), barium (Ba), and the like. Preferably, the chloride salt is sodium chloride (NaCl), and the carbonate salt is potassium carbonate ($K_2CO_3$). The aqueous salt solution may further comprise a polar compound to lower the surface tension thereby enhancing the wetting characteristics of the solution. Suitable polar compounds include denatured ethanol, isopropanol, xylene, and the like, as well as compositions comprising at least one of the foregoing polar compounds, of which denatured ethanol is preferred.

Treatment of the sensor includes dipping, spraying, wetting or any other method suitable for applying the aqueous salt solution to the sensor. The aqueous salt solution comprises chloride salts in a concentration of about 0.1 to about 1.5 moles/liter. Within this range, a concentration of less than or equal to about 1.25 moles/liter is preferred, with less than or equal to about 1.0 moles/liter is more preferred. Also preferred within this range is a concentration of chloride salts greater than or equal to about 0.25 moles/liter, with greater than or equal to about 0.50 moles/liter more preferred. The aqueous salt solution comprises carbonate salts in a concentration of about 0.1 to about 1.5 moles/liter. Within this range, a concentration of less than or equal to about 1.35 moles/liter is preferred, with less than or equal to about 1.25 moles/liter more preferred. Also preferred within this range is a concentration of carbonate salts of greater than or equal to about 0.25 moles/liter preferred, with greater than or equal to about 0.5 moles/liter more preferred. The treated sensor is then dried. Drying occurs at a temperature of greater than or equal to about 20° C., with a temperature of greater than or equal to about 50° C. preferred. Also preferred is a drying temperature of less than or equal to about 200° C., with a temperature of less than or equal to about 100° C. especially preferred.

Treatment of the sensor with the aqueous salt solution results in the first protective coating comprising an amount of chloride and carbonate salt mixture of about 0.1 to about 0.9 grams per cubic inch ($g/in^3$). Within this range, an amount of chloride and carbonate salt mixture of less than or equal to about 0.7 $g/in^3$ is preferred, with less than or equal to about 0.5 $g/in^3$ more preferred. Also preferred within this range is an amount of chloride and carbonate salt mixture in the first protective coating of greater than or equal to about 0.2 $g/in^3$, with greater than or equal to about 0.3 $g/in^3$ more preferred.

Disposed on a side of the first protective coating opposite the measuring electrode is a second protective coating. As with the first protective coating, the second protective coating may comprise a spinel (e.g., magnesium aluminate), alumina, zirconia, as well as combinations comprising at least one of the foregoing materials. Preferably, the second protective coating comprises high surface area alumina, including theta-alumina, gamma-alumina, delta-alumina, and the like, as well as combinations comprising at least one of the forgoing alumina; stabilized by rare earth or alkaline earth metal oxides, including lanthanum oxide, strontium oxide, barium oxide, calcium oxide, and the like, as well as combinations comprising at least one of the foregoing oxides. As with the first protective coating, the second protective coating may disposed using thin or thick film deposition techniques including sputtering, electron beam evaporation, chemical vapor deposition, screen printing, pad printing, ink jet printing, spinning, spraying, including flame spraying and plasma spraying, dip-coating and the like. The second protective coating has a thickness of up to about 500 μm, with less than or equal to about 400 μm preferred, and less than or equal to about 300 μm more preferred. Also preferred is the second protective coating having a thickness of greater than or equal to about 25 μm, with greater than or equal to about 75 μm more preferred, and greater than or equal to about 125 μm especially desired.

After deposition of the second protective coating, the sensor is heated. Heating occurs at a temperature less than or equal to about 800° C., with less than or equal to about 700° C. preferred. Also preferred is a heating temperature of greater than or equal to about 400° C., with greater than or equal to about 500° C. especially preferred. Heating is conducted for a duration of less than or equal to about 3 hours, with less than or equal to about 2 hours preferred, and less than or equal to about 1.5 hours most preferred.

The invention is further illustrated by the following non-limiting examples.

EXAMPLE 1

To test the effects of treatment on the sensor, three planar sensors were prepared. The first was treated with an aqueous chloride salt solution as follows: about 20 milligrams (mg) of aqueous 0.5 M chloride solution of Na, K and Li in equal proportions were dripped on the first protective coating, dried and then heated to 700° C. for 1 hour in air. The second was treated with an aqueous chloride and carbonate salt solution comprising 0.25 Molar (M) sodium chloride (NaCl) and 1.25M potassium carbonate ($K_2CO_3$), dried, and then heated to 700° C. for 1 hour in air. The aqueous salt solutions both further comprised 20% denatured ethanol to enhance wetting characteristics. The third was an untreated sensor.

The metal ink used in making the sensors consisted of platinum particles in the range of 0.2 to 0.5 micrometers, with roughly 2.5% yttria stabilized zirconia and appropriate organic vehicles so that the amount of platinum in the ink was between 58 wt. % and 65 wt. % with a target amount of 60 wt. %. The sensor element was then pressurized and heated to laminate the layers together, in accordance with the type of sensor. The sensor element is heated to a temperature of about 1475° C. to about 1550° C. for a sufficient period of time to fully sinter the layers, with a temperature of 1490° C. to about 1510° C. preferred, for a period of up to about 3 hours, with about 100 minutes to about 140 minutes preferred.

Figure 2:
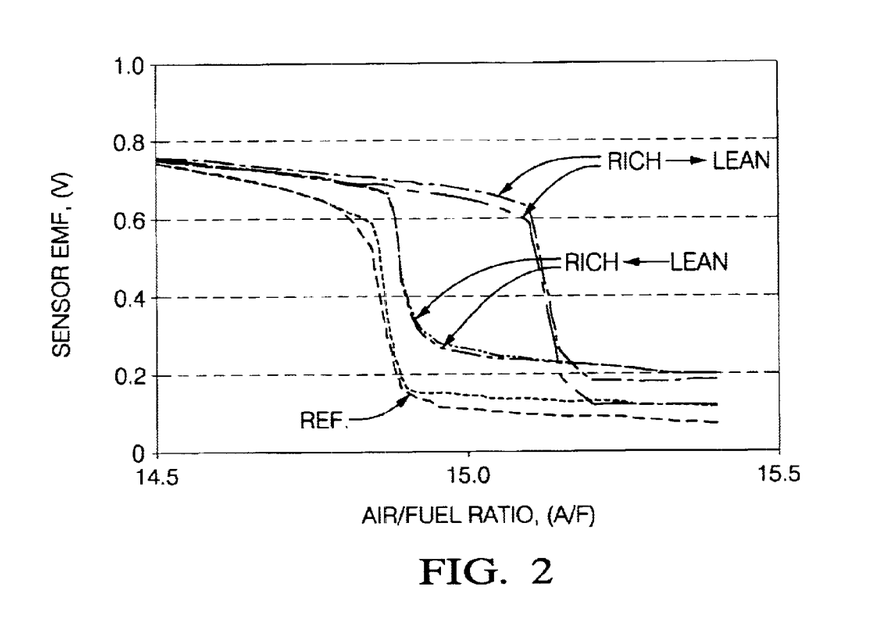
FIG. 2 is a graph showing sensor EMF versus air/fuel ratio of an unheated planar sensor without treatment.
Figure 3:
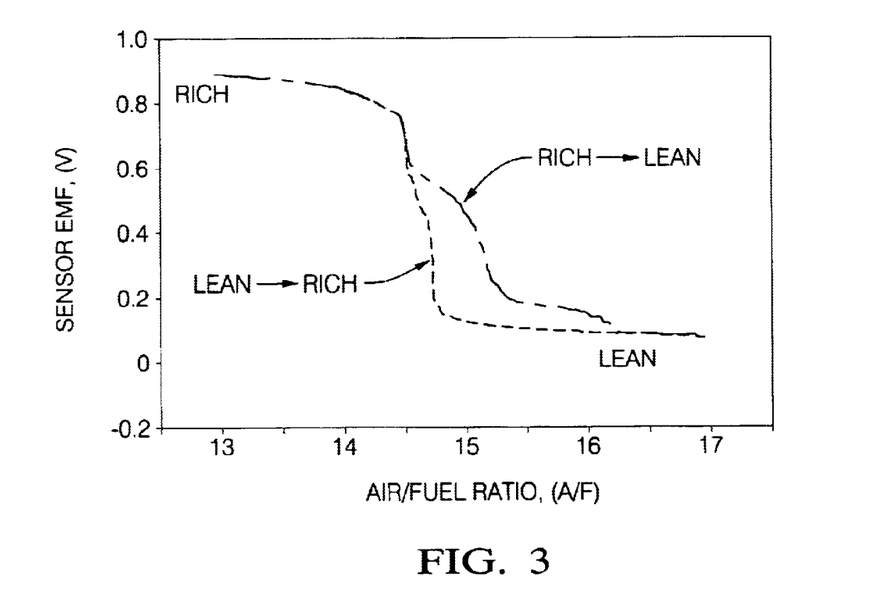
FIG. 3 is a graph showing sensor EMF versus air/fuel ratio of an unheated planar sensor after chloride treatment.
Figure 4:
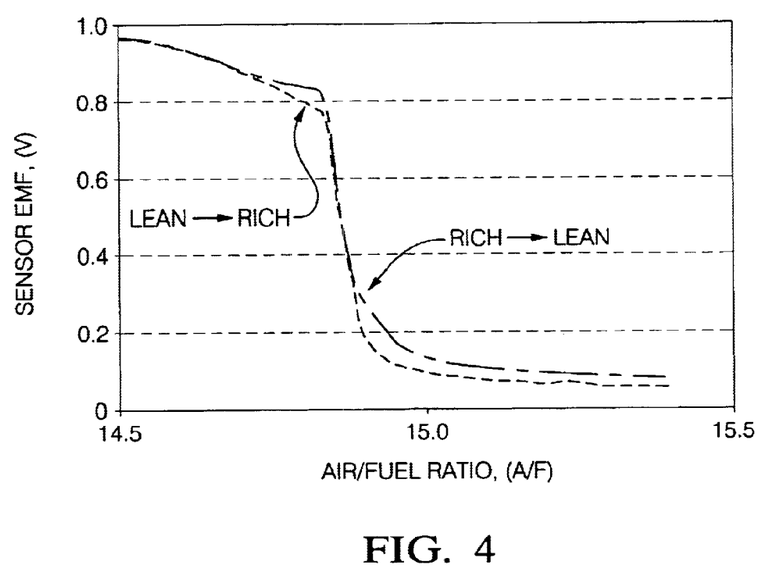
FIG. 4 is a graph showing sensor EMF versus air/fuel ratio of an unheated planar sensor after combined carbonate and chloride treatment.

FIG. 2 illustrates the switching characteristics of the untreated sensor at 440° C. on a gas bench using full feed gas. FIG. 3 shows the effect of chloride treatment in restoring the EMF and enhancing the rich to lean transition. FIG. 4 shows the effect of combined carbonate and chloride treatment in further enhancing the sensor EMF, rich to lean transition and the hysterisis in lean to rich and rich to lean transitions.

EXAMPLE 2

Eleven gas sensors were produced. Reference electrodes were applied to the inner surfaces of unsintered solid-state electrolyte bodies by coating the inner surfaces with a platinum ink suspension containing 0.5 weight percent (wt. %)-3.5 wt. % partially stabilized zirconia. Exhaust gas electrodes were next applied by coating the outer surfaces with platinum ink suspensions by a dip and dwell method which deposits the ink via a slip cast mechanism. The ink suspensions contain various combinations of partially stabilized zirconia (0.5 wt. %–3.5 wt. %), fully stabilized zirconia (1 wt. %–4 wt. %), ytrria (0.5 wt. %–1.0 wt. %), and carbon black (0 wt. %–2 wt. %), in the platinum inks. The percent solids of Pt in all inks were in the 15 wt. %–20 wt. % range.

After drying the electrodes at about 20° C. to about 200° C. for 30 minutes, an alumina protective coating was disposed on six of the eleven gas sensors. The coating was dried and all eleven elements were sintered at 1,500° C. to yield a sintered solid electrolyte body. Further, on the remaining five elements a porous protection layer for protecting the electrode against measurement gas was formed by plasma spraying alumina-magnesia spinel powder onto the surface of the electrode. After sintering, the electrodes were porous, uniform, and highly adherent. Finally, for additional protection, a dip-coating of ceramic, lanthanum-stabilized aluminum oxide ($Al_2O_3$), slurry was applied on all the sensors, dried, and then heated to 600° C. for 2 hours in air.

The sensor elements were then assembled and tested on a 3.8 Liter V6 engine.

Figure 6:
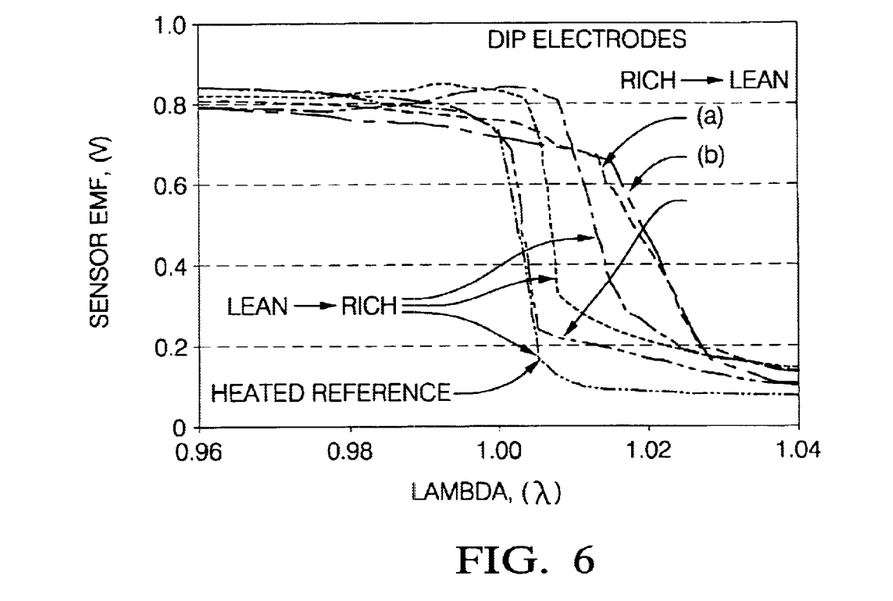
FIG. 6 is a graph showing sensor EMF versus lambda of two unheated conical sensors with co-fired metal ink electrodes including partially stabilized zirconia along with a heated reference sensor, all sensors were untreated.

FIG. 6 shows the switching characteristics of two co-fired sensor elements, both without treatment. One element has a dip-coated, co-fired protective coating and the other element has a plasma sprayed protective coating. Both sensors have a low-density ceramic coating over the first coating for additional protection. The metal ink contained 0.5 wt. %–2.5 wt. % partially stabilized zirconia, 0.5 wt. %–1.0 wt. % carbon black, and platinum powder suspended in denatured alcohol. As observed in FIG. 6, the sensor amplitude is comparable to a heated reference sensor but the characteristics are shifted toward leaner air/fuel ratios ($\lambda>1$), and are hysteretic due to asymmetry in rich to lean transitions in opposing directions.

Figure 7:
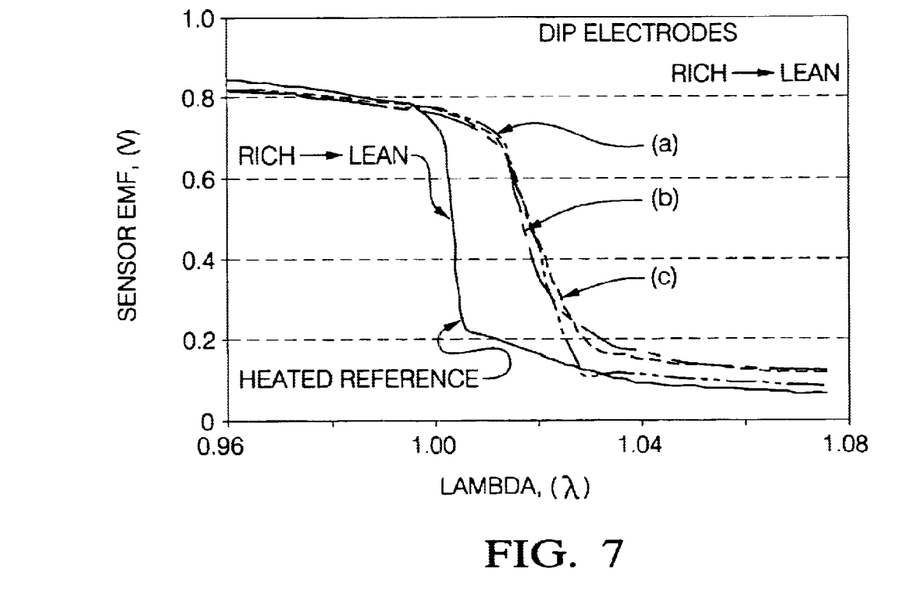
FIG. 7 is a graph showing sensor EMF versus lambda during rich to lean transition for three unheated conical sensors with co-fired metal ink electrodes including fully stabilized zirconia along with a heated reference sensor, all sensors were untreated.

FIG. 7 shows a comparison of rich to lean transitions for three untreated conical sensors with electrodes prepared with varied metal ink formulations. Two elements have a dip-coated, co-fired protective coating and the third element has a plasma sprayed protective coating. All sensors have a low-density ceramic coating over the first coating for additional protection. The metal ink contains 1 wt. %–4 wt. % fully stabilized zirconia, 0 wt. %–1.0 wt. % carbon black, and platinum powder suspended in denatured alcohol. As observed from FIGS. 6 and 7, the sensor response from both types of exhaust gas metal inks is similar, that is, lean shifted, hysteretic, and slower rich to lean transition than lean to rich transition.

Figure 5:
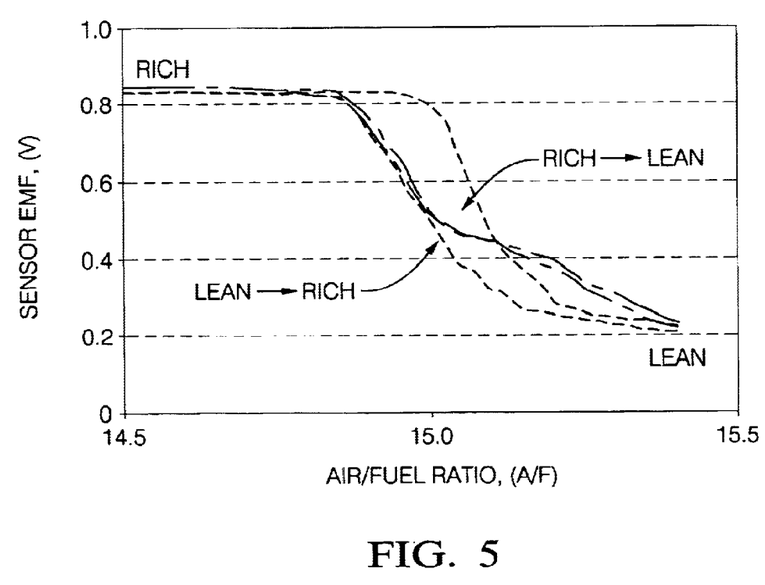
FIG. 5 is a graph showing sensor EMF versus air/fuel ratio of a conical sensor after carbonate treatment.

FIG. 5 illustrates sensor EMF versus air/fuel ratio of a conical sensor after carbonate treatment. The plot indicates that carbonate treatment of the sensor effectively reduces the amount of hysterisis experienced between lean to rich and rich to lean transitions.

Figure 8:
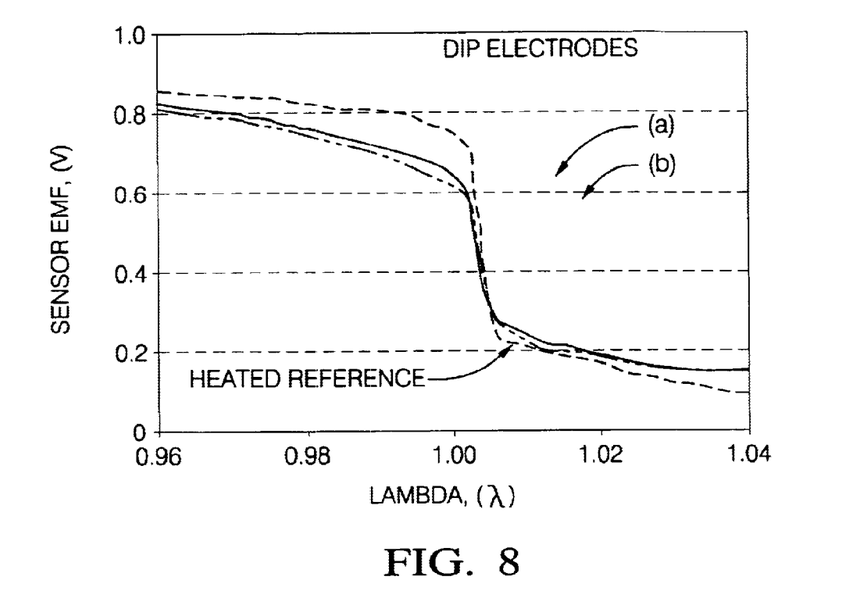
FIG. 8 is a graph showing EMF versus lambda during rich to lean transition for two unheated conical sensors with co-fired metal ink electrodes along with a heated reference sensor, after combined carbonate and chloride treatment.

FIG. 8 shows the switching characteristics of two co-fired sensor elements both with combined carbonate and chloride treatment. One element has a dip-coated, co-fired protective coating and the other element has a plasma sprayed protective coating. Both sensors have a low-density ceramic coating over the first coating for additional protection. The metal ink used to form the electrodes contains 0.5 wt. %–2.5 wt. % partially stabilized zirconia, 0.5 wt. %–1.0 wt. % carbon black, and platinum powder suspended in denatured alcohol. FIG. 8 shows that the combined carbonate and chloride treatment results in rich to lean transitions closely approximating that of the heated sensor.

Figure 9:
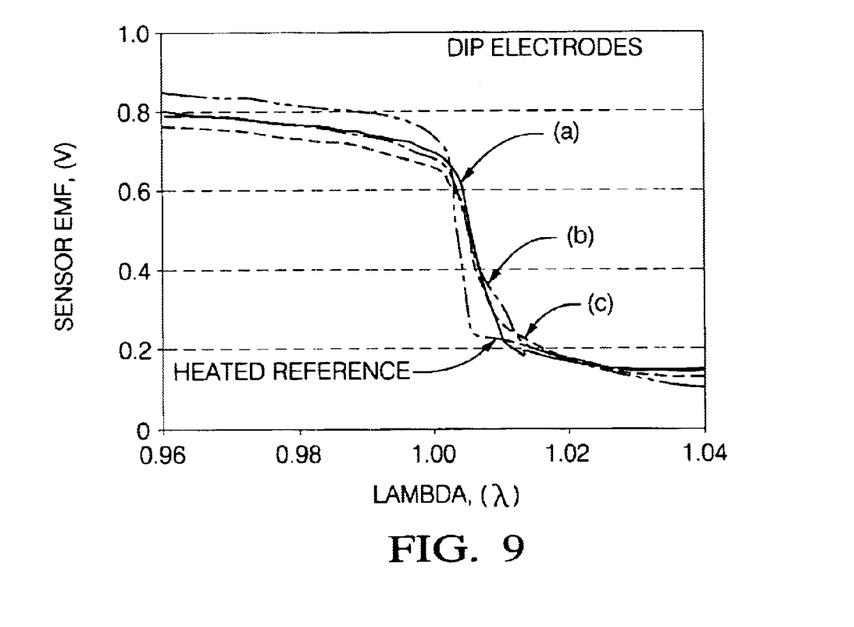
FIG. 9 is a graph showing EMF versus lambda during rich to lean transition for two unheated conical sensors with co-fired metal ink electrodes along with a heated reference sensor, after combined carbonate and chloride treatment.

Combined carbonate and chloride treatment with aqueous solutions comprising NaCl and $K_2CO_3$ significantly reduces the response time required for switching from rich to lean gas composition, improves rich to lean transition, and reduces hysterisis between lean to rich and rich to lean transitions. Therefore, the light-off time and low temperature (about 400° C.) performance of the unheated sensor is enhanced. The effect of carbonate treatment in reducing the hysterisis between the lean to rich and rich to lean transition was illustrated by treating one sintered element as follows: about 0.1 ml of aqueous 1.25 molar (M) potassium carbonate solution was used to wet the reference electrode and the exhaust gas electrode through the porous layer, dried, and platinum inks containing partially stabilized zirconia, carbon black, and yttria were applied. The engine performance of these unheated sensors at 400° C. exhaust gas for rich to lean transition was closer to a heated reference sensor. Similar benefits are observed in FIG. 9. FIG. 9 illustrates EMF versus lambda during rich to lean transition for two unheated conical sensors with combined carbonate and chloride treatment. The co-fired electrodes were formed by the application of a metal ink containing 1.0 wt. %–4.0 wt. % fully stabilized zirconia, 0 wt. %–1.0 wt. % carbon black, and platinum powder suspended in denatured ethanol. FIG. 9 shows that these treated sensors exhibit rich to lean transitions approximating the performance of a heated sensor.

Unheated sensors treated with aqueous salt solutions, especially those treated with combined carbonate and chloride salts advantageously achieve switching performance near stoichiometric air/fuel ratios comparable to a heated sensor. The treated sensors have high amplitude coupled with fast switching response times, and low light off times. The treated sensors exhibit a low level of impedance as evidenced by the sensor aptitude at 400° C. exhaust gas temperature. Treatment of the sensor reduces the effect of aging by increasing the sensor durability against exposures to toxic matter.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for producing a gas sensor, comprising:
   disposing a reference electrode on a side of an electrolyte;
   disposing a measuring electrode on a side of the electrolyte opposite the reference electrode;
   disposing a first protective coating on a side of the measuring electrode opposite the electrolyte;
   treating the sensor with an aqueous salt solution comprising chloride and carbonate salts comprising elements selected from the group consisting of Group IA and IIA elements of the Periodic Table to form a treated sensor comprising the chloride and the carbonate salt mixture;
   drying the treated sensor; and
   disposing a second protective coating on a side of the first protective coating opposite the measuring electrode.

2. The method of claim 1, wherein the chloride salt is NaCl.

3. The method of claim 1, wherein the carbonate salt is $K_2CO_3$.

4. The method of claim 1, wherein the treated sensor comprises about 0.1 to about 0.9 g/in³ chloride and carbonate salt mixture.

5. The method of claim 1, wherein the treated sensor comprises about 0.2 to about 0.7 $g/in^3$ chloride and carbonate salt mixture.

6. The method of claim 1, wherein the treated sensor comprises about 0.3 to about 0.5 $g/in^3$ chloride and carbonate salt mixture.

7. The method of claim 1, wherein the electrolyte is unsintered when the second protective coating is disposed on the first protective coating.

8. The method of claim 1, further comprising sintering the sensor.

9. The method of claim 1, wherein the second protective coating comprises a low-density ceramic.

10. A gas sensor produced from the method of claim 7.

11. A gas sensor, comprising:
   a reference electrode disposed on a side of an electrolyte;
   a measuring electrode disposed on a side of the electrolyte opposite the reference electrode;
   a first protective coating disposed on a side of the measuring electrode opposite the electrolyte, wherein the first protective coating comprises about 0.1 $g/in^3$ to about 0.9 $g/in^3$ of a salt mixture comprising chloride and carbonate salts comprising elements selected from the group consisting of Group IA and IIA elements of the Periodic Table; and
   a second protective coating disposed on a side of the first protective coating opposite the measuring electrode.

12. The sensor of claim 11, wherein the first protective coating comprises about 0.2 to about 0.7 $g/in^3$ of the salt mixture.

13. The sensor of claim 11, wherein the first protective coating comprises about 0.3 to about 0.5 $g/in^3$ of the salt mixture.

* * * * *